United States Patent [19]

Tsou et al.

[11] Patent Number: 4,681,968
[45] Date of Patent: Jul. 21, 1987

[54] METHOD OF PRODUCING ADIPONITRILE

[75] Inventors: Dean T. Tsou, Solon; Marc W. Blachman, Lyndhurst; James D. Burrington, Richmond Heights, all of Ohio

[73] Assignee: The Standard Oil Company, Cleveland, Ohio

[21] Appl. No.: 705,937

[22] Filed: Feb. 26, 1985

[51] Int. Cl.$^4$ .................. C07C 120/00; C07C 121/26
[52] U.S. Cl. ................................. 558/361; 558/363; 558/364
[58] Field of Search ............... 260/465.8 D; 558/361, 558/363, 364

[56] References Cited

U.S. PATENT DOCUMENTS

| 2,671,567 | 6/1972 | Onsager | 260/465.8 D |
|---|---|---|---|
| 3,644,477 | 2/1972 | Onsager | 260/465.8 D |
| 3,671,565 | 6/1972 | Yoo | 260/465.8 D X |
| 3,671,568 | 6/1972 | Onsager | 260/465.8 D |
| 3,729,498 | 4/1973 | Masada et al. | 260/465.8 D |
| 3,790,617 | 2/1974 | Masada et al. | 260/465.8 D |

FOREIGN PATENT DOCUMENTS

| 45-04048 | 2/1970 | Japan | 260/465.8 D |
|---|---|---|---|
| 46-17214 | 5/1971 | Japan | 260/465.8 D |
| 46-17218 | 5/1971 | Japan | 260/465.8 D |
| 46-17212 | 5/1971 | Japan | 260/465.8 D |
| 46-21369 | 6/1971 | Japan | 260/465.8 D |
| 46-39330 | 11/1971 | Japan | 260/465.8 D |
| 47-6290 | 2/1972 | Japan . | |
| 47-27917 | 10/1972 | Japan | 260/465.8 D |
| 50-142514 | 11/1975 | Japan . | |
| 1177059 | 1/1970 | United Kingdom | 260/465.8 D |
| 1398089 | 6/1975 | United Kingdom | 260/465.8 D |

OTHER PUBLICATIONS

Cotton et al.; Advanced Inorganic Chemistry, 4th Ed.; John Wiley & Sons; pp. 619–620–621, no date available.
Hawley; The Condensed Chemical Dictionary, 8th Ed. (1971), pp. 882 and 487; Van Nostrand Reinhold Co.
Agnes, et al.; Chemical Communications, 1968, p. 1515.
Druliner, et al.; J. of Organometallic Chem., 240 (1982); pp. 277, 278, 280, 281, 282, 283.

Primary Examiner—Joseph Paul Brust
Attorney, Agent, or Firm—Charles S. Lynch; John E. Miller; Larry W. Evans

[57] ABSTRACT

A first row transition metal catalyzed procedure for the production of adiponitrile from acrylonitrile comprising mixing a first row transition metal salt, acrylonitrile, metallic reducing agent and solvent, heating the solution, and adding a quench solution to the mixture comprising a proton donor material having a $0<\text{pk}_a<12$ and an organic amide solvent for the proton donor material. Preferably, an organic ligand is added to the solution prior to heating and adding the quench solution.

12 Claims, 2 Drawing Figures

METHOD OF PRODUCING ADIPONITRILE

BACKGROUND OF THE INVENTION

The present invention is directed to a method for the production of adiponitrile from acrylonitrile. In particular, the present invention is directed to a method of producing adiponitrile from acrylonitrile utilizing a first row transition metal catalyst such as cobalt.

Cobalt mediated acrylonitrile hydrodimerization to adiponitrile was reported in the literature in the late 1960's. The reaction was a two-step process broadly involving (1) mixing acrylonitrile, cobalt chloride and a reducing agent such as manganese powder in dimethylformamide and heating the solution and (2) adding a quenching reagent such as water or hydrogen sulfide to the solution. It was postulated that the first step involved the reduction of cobalt$^{2+}$ to a lower oxidation state. This reduced cobalt metal then coordinated with two molecules of acrylonitrile, forming an intermediate complex. In the second step, the quenching (terminating) of the intermediate occurred with either water or hydrogen sulfide. The two-step process is best illustrated by the two equations appearing below:

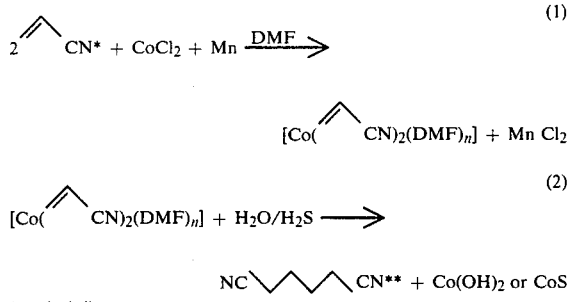

*acrylonitrile
**adiponitrile

As shown in the above equations, this method resulted in the desired dimer, adiponitrile (ADP), and either cobalt hydroxide or cobalt sulfide, depending on which quench agent was used. The disadvantage of this procedure is that these cobalt species are unreactive toward further acrylonitrile dimerization. That is, these reactions produce inactive cobalt species thereby limiting the reaction to one that, at best, yields only a stoichiometric amount of dimer when compared to cobalt.

Subsequent investigators attempted to study the cobalt metal mediated acrylonitrile dimerization process in more detail. Alternate reducing agents (manganese, magnesium, or zinc), solvents (dimethylformamide, acetonitrile, ethanol, or benzene) and quenching reagents were tested. In all cases the selectivity to adiponitrile was generally high (over 90%), however, the turnover number (# molecule ADP produced/# molecules cobalt used) never went above 1. That is, the reaction was stoichiometric in the cobalt (one molecule) used compared to the amount of adiponitrile produced (one molecule). Finally, investigators discovered that the slow addition of a quench solution comprising an ammonium chloride/methanol solution produced a system which was catalytic. That is, the turnover number (ADP/cobalt) increased from 1 to the range of about 3.5 to 4.5 with an adiponitrile selectivity in the range of 30 percent. As can be readily seen, the selectivity to adiponitrile was lowered dramatically when the reaction was made catalytic to cobalt.

In summary, the linear hydrodimerization of acrylonitrile to adiponitrile by cobalt-based systems has been reported in the literature. Moreover, the reaction can be made catalytic in cobalt by slow addition of a quench solution comprising ammonium chloride and methanol. This quench method has resulted in ADP/cobalt turnover numbers of approximately 4 with selectivity to ADP of about 30 percent. The present invention is directed to the development of a cobalt promoted dimerization process for the production of adiponitrile from acrylonitrile which substantially improves the ADP/cobalt turnover number while simultaneously increasing the selectivity of the reaction to adiponitrile.

SUMMARY OF THE INVENTION

It is the primary object of the present invention to provide a process for producing adiponitrile from acrylonitrile by utilization of a first row transition metal catalyst.

It is another object of the present invention to provide a process for producing adiponitrile from acrylonitrile by utilizing a Group VIII first row transition metal catalyst.

It is still another object of the present invention to provide a cobalt catalyzed adiponitrile production procedure having a high turnover number (ADP/cobalt) and increased selectivity to adiponitrile.

Additional objects, advantages and novel features of the invention will be set forth in part in the description which follows, and in part will become apparent to those skilled in the art upon examination of the following, or may be learned by the practice of the invention. The objects and advantages of the invention may be realized and attained by means of the instrumentalities and combinations particularly pointed out in the appended claims.

To achieve the foregoing and other objects and in accordance with the purpose of the present invention as embodied and further described herein, the process of the present invention comprises mixing a first row transition metal salt, a metallic reducing agent, acrylonitrile and a suitable solvent (e.g., amide solvent) in a container to form a first solution; heating this solution for a time sufficient to form an active transition metal complex; adding a quench solution to the first solution to free the transition metal from the complex to produce adiponitrile, the quench solution comprising a proton donor material having a $0 < pk_a < 12$ and an organic amide solvent for the donor material. Preferably, the organic amide is selected from the group consisting of dimethylformamide and dimethylacetamide.

In a preferred embodiment of the process of the present invention an organic ligand complex of the formula comprising $R_3'E$ where $E = N$, P, As, Sb or Bi and $R' =$ alkyl, phenyl, alkoxyl, phenoxy, substituted alkyl or aryl or any combination thereof, is added to the first solution. Preferably, the organic ligand complex is triphenylphosphine. Most preferably, the ratio of E:transition metal in the first solution is about 2.

In another preferred embodiment of the process is the present invention, the quench solution further comprises methanol where the mole ratio of methanol to the proton donor material is no greater than 2.

In still another preferred embodiment of the present invention, the transition metal salt is selected from the group consisting of metal halides, metal organic acid salts, metal phosphates and metal acetylacetonates. More preferably, the first row transition metal is selected from Group VIII. The especially preferred transition metal is cobalt and the especially preferred transition metal salt is cobalt chloride.

In a further preferred embodiment of the present invention the metallic reducing agent is selected from the group consisting of manganese, magnesium and zinc. Most preferably, the metallic reducing agent is manganese.

In a still further preferred embodiment of the present invention the proton donor material is a tertiary organic Group VB salt having the formula $R_3AH^+X^-$ where A=N, P, As, Sb, and Bi; X=Cl, Br, I, $ClO_4$, $BF_4$, $NO_3$ and $SO_4$ and R=alkyl, aryl, phenyl, substituted alkyl or aryl or any combination thereof. Most preferably A=N or P; X=Cl and R is an alkyl group, in particular, butyl.

In a further preferred embodiment of the present invention the concentration of the acrylonitrile and transition metal salt in the first solution is in the range of about 0.1M to 8M and about 0.01M to 3M, respectively. Most preferably, the acrylonitrile concentration is about 3M and the transition metal salt concentration is about 0.1M.

In a still further preferred embodiment of the present invention the quenching solution is added at a rate of between 0.01 to 1 ml/min. Most preferably, the rate of addition of the quench solution is about 0.04 ml/min.

In another preferred embodiment of the present invention the heating of the first solution is for a period of about 1 hour.

In still another further preferred embodiment of the present invention the concentration of the proton donor material in the quench solution is in the range of 0.1 to 5M and the concentration of the methanol in the quench solution is in the range of 0.1 to 5M. Most preferably, the concentrations of methanol and proton donor material in the quench solution are about 1M.

The first row transition metal catalyzed procedure of the present invention provides several distinct advantages over the methods previously described in the literature. Applicants have discovered that the excess methanol present in the quench solutions previously discussed has an adverse effect on the reaction. Accordingly, applicants' invention is directed broadly to the elimination of all methanol or at least the excess methanol from the quench solution to obtain a more efficient reaction. Applicants' procedure involves replacement of the ammonium chloride salt with a proton donor material having a high solubility in an amide solvent such as dimethylformamide or dimethylacetamide. This substitution enables one to reduce or eliminate the methanol from the quench solution. The resulting procedure results in an acrylonitrile hydrodimerization procedure having an improved turnover number (ADP/Co) and selectivity to adiponitrile. In addition, applicants have discovered that the addition of an organic ligand complex to the first solution during the formation of the active transition metal complex (i.e., cobalt) further improves the turnover number (approximately 11) while increasing selectivity to adiponitrile (about 83 percent). Accordingly, applicants' process provides a distinct and significant economic improvement over the procedures of the prior art which were characterized by turnover numbers of about 4 and selectivity of about 30 percent.

BRIEF DESCRIPTION OF THE DRAWINGS

The accompanying drawings, which are incorporated in and form a part of the specification, illustrate the preferred embodiments of the present invention and, together with description, serve to explain the principles of the invention.

In the drawings.

Figure 1:
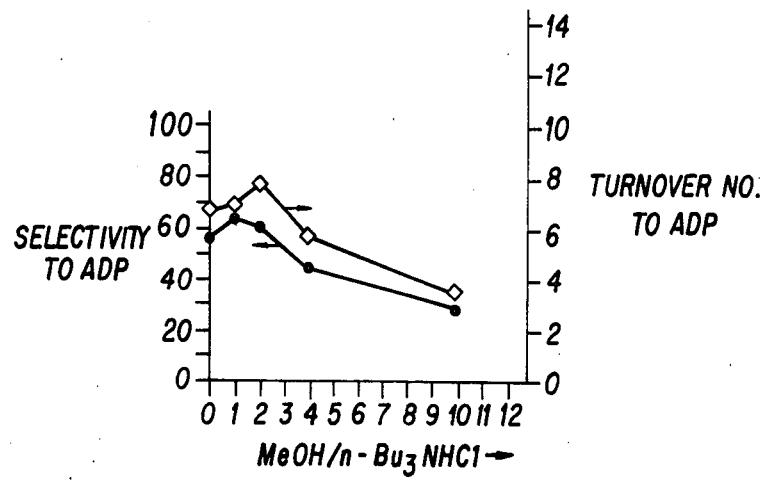
FIG. 1 is a graph illustrating the effects of methanol on the turnover number for a cobalt catalyzed process in accordance with the present invention.

Reference will now be made in detail to the present preferred embodiment of the invention, the results of which are detailed in the accompanying drawings.

DETAILED DESCRIPTION OF THE INVENTION

The process of the present invention comprises mixing a first row transition metal salt, a metallic reducing agent, acrylonitrile, and a solvent in a container to form a first solution, heating this solution for a time sufficient to form an active transition metal complex, and adding a quench solution comprising a proton donor material having $0 < pk_a < 12$ and an organic amide solvent for the proton donor material to the first solution to liberate the transition metal and produce adiponitrile. Preferably, the process is performed under an inert atmosphere such as argon and nitrogen.

Typically, the heating of the first solution is in the range of 25° to 150° C. for about 1 hour. In the case of cobalt salts, the solution turns red during this heating step.

Preferably, the first row transition metal is selected from Group VIII of the Periodic Table (i.e., Fe, Ni, Co). Most preferably, the transition metal is cobalt. The metal salt may comprise metal halides, metal organic acid salts, metal phosphates and metal acetylacetonates. Most preferably, the transition metal salt is a cobalt halide. The concentration of the transition metal salt in the first solution is in the range of 0.01M to 3M. Most preferably, the concentration of the transition metal salt is about 0.1 M.

The metallic reducing agent present in the first solution may be selected from the group consisting of Mg, Zn, Mn. The exact amount of metallic reducing agent used in the first solution is not critical except that it should be present in an amount sufficient to regenerate the transition metal to its active state. The preferred metallic reducing agent is Mn.

The concentration of the acrylonitrile in the first solution may range from about 0.1 to 8M. The most preferred acrylonitrile concentration being about 3M.

The usual solvent utilized in the first solution is dimethylformamide. However, any suitable organic amide solvent suitable for purposes of this process may be utilized such as dimethylacetamide.

Preferably, the first solution also contains an organic ligand complex having the formula $R_3'E$ where:

E=P, N, As, Bi and Sb; and

R'=alkyl, aryl, substituted alkyls or aryls, phenyl or any combination thereof.

Most preferably, the organic ligand complex is triphenylphosphine. Moreover, a preformed transition metal salt-organic ligand complex (e.g., CoCl$_2$-Triphenylphosphine) may be utilized in the process of the present invention.

In addition, the concentration of the organic ligand complex present in the first solution should be in an amount so that the ratio of E:transition metal (e.g., Co) is no greater than 2. It has been found that if the ratio of E:transition metal is in excess of 2 the E component reduces the cobalt catalyst activity by blocking coordination cites needed for the dimerization reaction. In addition, the E component catalyzes acrylonitrile oligomerization and, therefore, any significant excess results in a significant reduction in selectivity to adiponitrile.

The quench solution should be added slowly to the heated solution, usually at the rate of about 0.1 ml to 1 ml/min. While the quench solution is added, the first solution is normally maintained at the elevated temperature and heating is continued for up to 25 hours to complete the reaction. The solution is then treated by conventional techniques known in the art to recover adiponitrile (e.g., filtration or distillation).

Preferably, the quench solution comprises a proton donor material having a $0 < pk_a < 12$ and an organic amide solvent. Most preferably, the quench solution can also include some methanol. However, the mole ratio of methanol to proton donor material should be not greater than 2. Typically, the concentration of the proton donor material is between 0.1M to 5M and the concentration of methanol in the quench solution is also between 0.1M to 5M.

Preferably, the proton donor material used in the quench solution is a tertiary organic Group VB salt of the formula:

$$R_3AH^{30}X^-$$

where
R = alkyl, aryl, phenyl, substituted alkyl or aryl or combinations thereof;
A = N, P, As, Sb or B;
X = Cl, Br, I, ClO$_4$, BF$_4$, NO$_3$, and SO$_4$.
Most preferably, R = alkyl, in particular butyl; A = N or P, and X = a halide, in particular Cl. Especially preferred as a proton donor material is tributyl-ammonium chloride.

While the above salts are preferred for the proton donor material, it should be understood that the present invention is not limited to these classes of materials. Any proton donor material which would allow elimination or control of the amount of alcohol (i.e., methanol) present in the quench solution is within the scope of the present invention. For example, pyridinium salts, phenols, organic imides and carboxylic acids may be utilized in the practice of the present invention.

Any organic amide material that is a solvent for the proton donor material is suitable in the practice of the present invention. In particular, dimethylformamide and dimethylacetamide are the preferred amide solvents utilized.

To further illustrate the method of the present invention, the following examples are presented.

EXAMPLE 1

2.0 g of manganese and 2.0 ml of acrylonitrile and 0.6 g of cobalt chloride were placed into a 50 ml flask containing 10 ml of DMF. The ingredients were heated in the flask under argon to 60° C. with vigorous stirring. After 1 hour the quench solution (1M tributyl-ammonium chloride and 1M methanol in dimethylformamide) was added slowly at the rate of 0.04 ml/per minute. After 21 hours the reaction mixture is analyzed by gas chromatography. 8.5 mmole of adiponitrile is obtained representing a 65 percent selectivity and a 6.9 turnover number.

The effect of different amounts of methanol used in the quench solution on the selectivity and turnover number is shown in FIG. 1. As can be seen from the graph of FIG. 1 as the mole ratio of methanol to tributyl-ammonium chloride increases, the turnover number and selectivity of the process decreases. Accordingly, the mole ratio of methanol to tributyl-ammonium chloride preferably is maintained at 2 or lower.

EXAMPLE 2

The present example shows the effect of the organic ligand complex upon the turnover number and selectivity of the process of the present invention.

2 g of manganese, 2 ml of acrylonitrile and 0.6 g of cobalt chloride and 0.64 g of triphenylphosphine were placed in a 50 ml flask containing DMF and dissolved under argon. The flask was heated to 60° C. and the solution was stirred vigorously. After 1 hour the quench solution (1M in tributyl-ammonium chloride and 1M in methanol in dimethylformamide) is added slowly at the rate of 0.04 ml/per minute. After 22 hours the reaction mixture is analyzed by gas chromatography. 13.0 mmoles of adiponitrile is obtained representing an 83 percent selectivity in a 10.9 turnover number.

Figure 2:
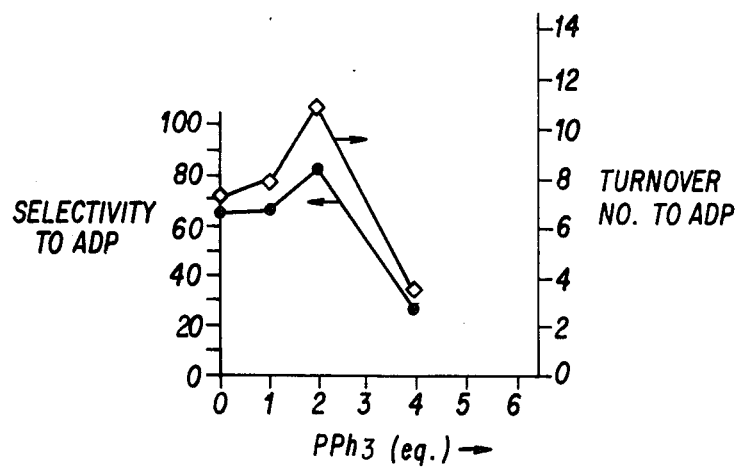
FIG. 2 is a graphical representation showing the effect of the addition of the organic ligand on a cobalt catalyzed process in accordance with the present invention.

The results obtained from the process of Example 2 are graphically illustrated in FIG. 2 which also shows the effect of the addition of excess organic ligand complex (triphenylphosphine) to the reaction. As can be seen from FIG. 2, when excess organic ligand is added the selectivity and turnover number rapidly decrease. Accordingly, for optimum results the ratio of organic ligand complex to cobalt should be kept at approximately 2.

A comparison of the results of Example 1 and 2 with the prior literature procedures (quench solution comprising ammonium chloride and methanol) shows that a significant improvement in selectivity and turnover rate is achieved with the process of the present invention. The prior procedures were only able to obtain a turnover number (ADP/Co) in the range of 4 with a selectivity of only a 30 percent adiponitrile. Applicants' procedure obtains a selectivity of 65 percent or more and a turnover number of almost 7. In applicants' preferred embodiment the turnover number is approximately 11 and selectivity to adiponitrile is 83 percent. These results illustrate significant improvement over the prior procedures.

The foregoing description of the preferred embodiments of the present invention has been presented for purposes of illustration and description. It is not intended to be exhaustive or to limit the invention to the precise form disclosed, and obviously many modifications and variations are possible in light of the above teaching. The embodiments were chosen and described in order to best explain the principles and the invention in its practical application to thereby enable others skilled in the art to best utilize the invention and various embodiments and with various modifications as are suited to the particular use contemplated. It is intended that the scope of the invention be defined by the claims appended hereto.

What is claimed is:

1. In a process for the production of adiponitrile from acrylonitrile comprising:
   (a) mixing a first row transition metal salt, a metallic reducing agent selected from Mg, Mn and Zn, acrylonitrile and an organic amide solvent to form a first solution;
   (b) heating said first solution for a time sufficient to form an active transition metal complex; and
   (c) adding a quench solution to said first solution to liberate said transition metal from said complex and produce adiponitrile, said quench solution comprising a proton donor material having $0 < pk_a < 12$ and an organic solvent for the proton donor material, the improvement wherein said quench solution comprises an organic proton donor dissolved in an organic amide solvent, wherein said quench solution contains from zero up to a maximum of 2 moles of methanol per mole of proton donor.

2. The improvement of claim 1 wherein said solvent in steps (a) and (c) is independently selected from dimethylformamide and dimethylacetamide.

3. The improvement of claim 2 wherein said proton donor comprises tributyl-ammonium chloride.

4. The improvement of claim 1 wherein said transition metal is selected from Group VIII of the periodic table.

5. The improvement of claim 4 wherein said transition metal is cobalt.

6. The improvement of claim 5 wherein said transition metal salt is cobalt chloride.

7. The improvement of claim 3 wherein said transition metal is selected from Group VIII of the periodic table.

8. The improvement of claim 7 wherein said transition metal is cobalt.

9. The improvement of claim 8 wherein said transition metal salt is cobalt chloride.

10. The improvement of claim 2 wherein said transition metal is selected from Group VIII of the periodic table.

11. The improvement of any one of claims 2, 3, 4, 5, 6, 7, 8, 9, or 10 said first solution further comprises an organic ligand complex characterized by the formula:

$$R'_3E$$

where each R' is independently selected from alkyl, aryl, alkoxyl, phenoxy, and combinations thereof, and
   E is selected from P, As, N, Sb, and Bi.

12. The improvement of any one of claims 2, 3, 4, 5, 6, 7, 8, 9, or 10 wherein said first solution further comprises an organic ligand complex characterized by the formula:

$$R'_3E$$

where each R' is independently selected from alkyl, aryl, alkoxyl, phenoxy, and combinations thereof, and
   E is selected from P, As, N, Sb or Bi and wherein the ratio of E:transition metal in said first solution is not greater than about 2.

* * * * *